United States Patent [19]

Mueller

[11] Patent Number: 4,878,903

[45] Date of Patent: Nov. 7, 1989

[54] PREFILLED CATHETER TIP SYRINGE KIT

[76] Inventor: Louis H. Mueller, 165 Sheffield Cir., Palm Harbor, Fla. 34683

[21] Appl. No.: 182,259

[22] Filed: Apr. 15, 1988

[51] Int. Cl.$^4$ .............................................. B65D 83/10
[52] U.S. Cl. ................................... 604/199; 206/364
[58] Field of Search ....................... 206/363, 364, 438; 604/187, 199, 207, 218, 280, 403; 128/655

[56] References Cited

U.S. PATENT DOCUMENTS

| | | | |
|---|---|---|---|
| 2,804,969 | 9/1957 | Barnett | 206/363 |
| 3,093,242 | 6/1963 | Huyck et al. | 206/364 |
| 3,186,628 | 6/1965 | Rohde | 206/364 |
| 3,473,646 | 10/1969 | Burke | 206/364 |
| 3,642,123 | 2/1972 | Knox | 604/199 |
| 3,937,219 | 2/1976 | Karakashian | 604/199 |
| 4,226,328 | 10/1980 | Beddow | 206/364 |
| 4,811,847 | 3/1989 | Reif et al. | 206/366 |

FOREIGN PATENT DOCUMENTS 0227401 1/1987 European Pat. Off. ............ 128/655

Primary Examiner—Dalton L. Truluck
Assistant Examiner—Denise W. DeFranco
Attorney, Agent, or Firm—Eugene E. Renz, Jr.

[57] ABSTRACT

An irrigation kit for catheter irrigation and a prefilled piston syringe containing sufficient fluid for a unitary catheter irrigation. The syringe includes a catheter tip sized to operably connect to a conventional catheter tube and a cap on the tip removably mounted to selectively prevent escape of the fluid from the syringe when the tip is place. The kit further includes a disposable pouch for enclosing the filled syringe, the pouch and the filled syringe being sterilized after enclosure of the syringe herein.

3 Claims, 1 Drawing Sheet

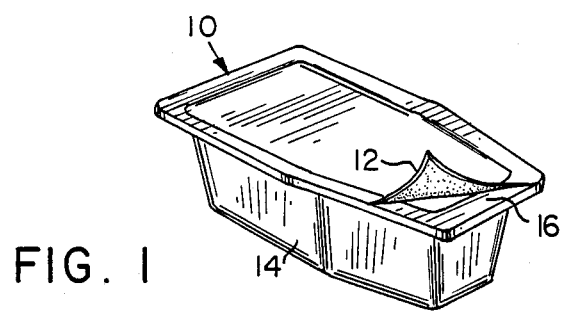
FIG. 1
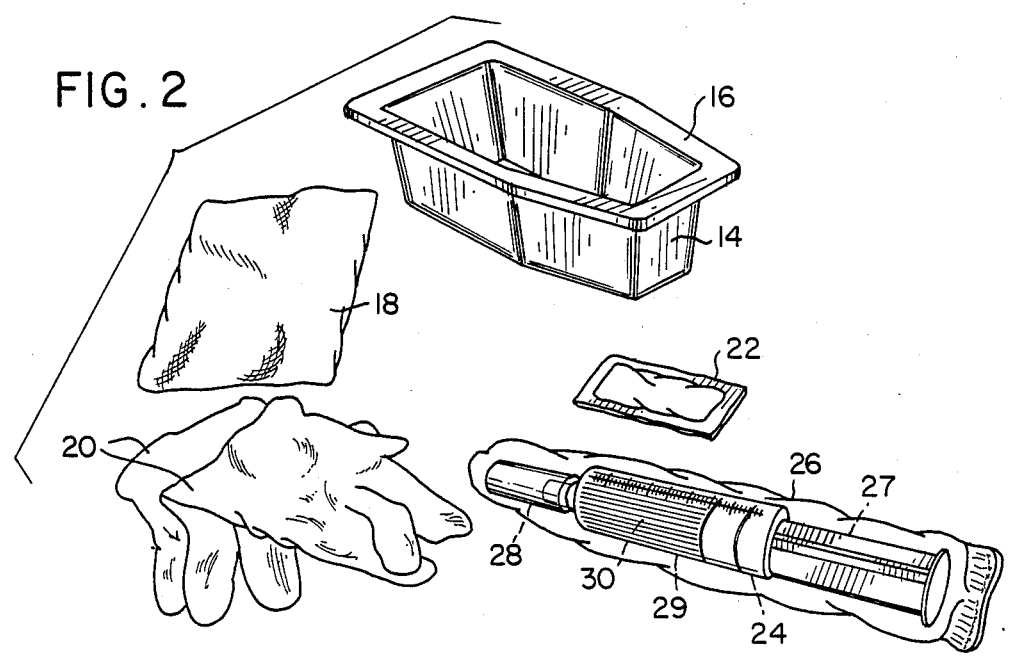
FIG. 2
FIG. 3
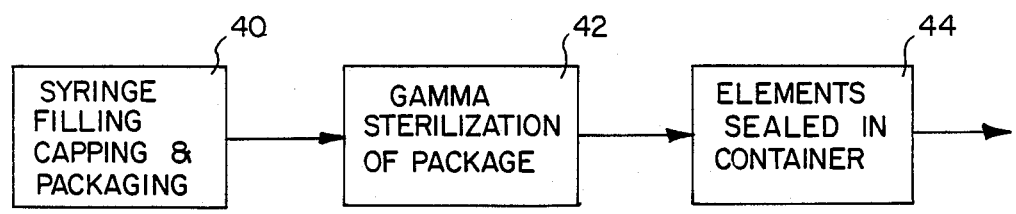

PREFILLED CATHETER TIP SYRINGE KIT

FIELD OF THE INVENTION

This invention relates to equipment used for catheter irrigation and more particularly to a device in which a unit dose of sterile water or saline solution or dilute acetic acid solutions are injected into catheters for irrigation thereof.

BACKGROUND OF THE INVENTION

For at least the past several hundred years, catheters have been irrigated by a procedure in which a quantity of irrigating solution is withdrawn from a supply of that solution, usually with a piston type syringe and usually in an amount ranging from perhaps less than 45 cc to as much as 75 cc followed by application of the solution to the catheter. A typical irrigation dosage is approximately 60 cc. Normal procedure involves taking a sterilized catheter tip syringe, filling the syringe from a supply bottle which may or may not be sterile since it cannot be protected once it has been opened, and using the filled syringe to irrigate the catheter.

In the traditional method of performing an irrigation procedure, a separate bottle of irrigation solution is used to pour a quantity of the fluid into a plastic graduate cylinder. Then the syringe is used to withdraw the irrigation solution from the graduate, to be used as described to irrigate the catheter.

While this procedure has been employed for a very long period of time, it is not without problems. Specifically, there is a small but real percentage of incident where there has been cross contamination due to the re-use of equipment. Particularly when there are multiple uses from the same bottle of irrigation solution, cross contamination can occur. Hepatitis is relatively easily transmitted because it is possible that the virus could somehow contaminate the solution, due to the contact with the patient by the catheter. AIDS, of course, is a concern, although the disease is not presently considered to be nearly as contagious as hepatitis under these particular treatment circumstances.

It is not often that a medical procedure changes after long periods of continued use. Nevertheless, it would be extremely useful if a device could be provided which would be suitable for irrigation procedures for catheters and which would avoid possible contamination of irrigation solutions. An object of this invention is to provide a device which would permit a quick, efficient, and totally safe catheter irrigation procedure.

Another object of this invention is to provide a unitary system which can be pre-sterilized and stored in a simple container in a ready to use condition so that effective treatment can be applied as needed and when needed. Often times Doctors are present during this procedure and a quick, easy to use self-contained device would save considerable time and expense.

SUMMARY OF THE INVENTION

It has not been discovered that an improved medical procedure may be employed for the irrigation of catheters with a sterile solution. The invention comprises a device which may be used as an irrigation kit for catheter irrigation. The device includes a prefilled piston syringe containing sufficient fluid for a unitary catheter irrigation. The syringe includes a catheter tip which is sized to operably connect to a conventional catheter tube. A cap is placed on the tip and is removably mounted to selectively prevent escape of fluid from the syringe once it has been filled. The kit further includes a disposable pouch which encloses the filled syringe so that the syringe and pouch may be sterilized and maintained in that sterile condition until it is needed for use.

The sterilized pouch is contained in a sealed rigid container and may further include sterilized gauze and an application pad. The syringe will contain from about 45 cc to about 75 cc of irrigation fluid. Typical irrigation fluids are sterile water, normal saline solutions and dilute aqueous acid solutions. Saline solutions normally contain less than about 1% sodium chloride and typically contains 0.9% sodium chloride. Dilute aqueous acid solutions are normally made up of about 0.25% of acetic acid.

The kit, whether or not included in a container, has been sterilized in order to provide irrigation treatment without concern for contamination of the patient. A preferred method for sterilizing the filled syringe enclosed in the disposable pouch is to use a gamma radiation source for sterilization.

BRIEF DESCRIPTION OF THE DRAWINGS

These and other objects of the present invention and the various features and details of the operation and construction thereof are hereinafter more fully set forth with reference to the accompanying drawings, wherein:

FIG. 1 is a perspective view of the kit, showing the peel away feature of a preferred embodiment;

FIG. 2 is a perspective view showing various components of the preferred embodiment, including the preferred syringe and pouch;

FIG. 3 is a block diagram illustrating the preferred method for producing the embodiment shown in FIGS. 1 and 2.

DETAILED DESCRIPTION OF THE PREFERRED EMBODIMENT

As shown in FIG. 1, the general reference numeral 10 describes a sealed container 14 which has a cover 12 which is attached, by adhesive or heat sealing to the upper terminal sealing flange 16. The plastic tub 14 is sufficiently rigid to prevent the tub from collapsing under normal conditions of handling and storage. Ideally, the tubs are suitable for stacking so that they may be conveniently packaged and shipped in bulk, and stored in a convenient place for use when needed.

The adhesively or heat sealed tear off cover 12 can also contain printed instructions for use of the kit, along with any precautionary warnings, labeling that is required, and other information. Removal of the tear off cover permits access to the remainder of the kit, which in its simplest form may only contain a prefilled syringe in a disposable pouch. As shown in FIG. 2, however, a gauze pad 18, and an alcohol preparation pad 22, sealed in a foil package, all may be inclued within the plastic tub 14 as part of a complete supply of the equipment necessary for catheter irrigation.

A piston type syringe shown generally by reference 24 is prefilled in sanitary laboratory or factory conditions with an appropriate solution for use as a catheter irrigation solution. Preferred are, of course, the typical treatment solutions are saline solutions which normally contain less than about 1% sodium chloride. A highly preferred saline solution is normal saline solution which contains 0.9% sodium chloride. Also preferred as an irrigation solution is sterile water. Additionally, dilute aqueous acid solutions are also preferred, particularly those solutions of about 0.25% acetic acid in distilled water. Filling is accomplished by pulling the piston 27 back from the barrel 30 when the tip of the syringe 24 is in a fluid of the type to be used for catheter irrigation. After the fluid 30 fills the barrel 29, so that a predetermined quantity of irrigation fluid is present, a cap 28 is placed on the catheter tip of the barrel 29 to selectively prevent escape of the fluid 30 from the syringe 24.

When the syringe 24 is contained within the pouch 26, it is protected from inadvertent contamination or damage. For example, the pouch could be dropped without concern for damage, since the tip of the syringe is protected by the cap 28 and the fluid 30 within the barrel 29 will prevent plunger 27 from moving inwardly.

It is intended that the syringe 24 and the pouch 26 will be sterilized after the pouch 26 has been sealed. Sterilization can be accomplished in a variety of ways, but gamma ray sterilization is the preferred method. Using the gamma ray method of sterilization, the entire inside of the pouch is cleansed of any contamination. The fluid 30 contained within the barrel 29 will be capable of performing its intended function of cleansing the catheter without any danger of transmitting undesirable contamination to the patient being treated.

As shown in FIG. 3, the process for preparing the irrigation kits of the present invention comprises filling the syringe and capping it, followed by packaging the capped syringe in a polyfilm pouch. After these steps in block 40, the filled enclosed syringe is sterilized in block 42 by gamma ray sterilization so that the interior is completely free from contamination and remains such until the disposable pouch is opened. At this point, the filled sterile package syringe is placed in the plastic tub 14 along with other equipment such as pads, alcohol, prep pads and the like. The addition of a peel off cover 12 completes the sealing process shown in block 44.

When it is time to use the device of the present invention, a sealed container 10 will be taken from the appropriate stored location, such as in the patent's room or the like. The peel off tab 12 will be removed, exposing a gauze pad 18, and an alcohol preparation pad 22. This latter pad is available in a sealed foil package as shown in the FIG. 2.

A syringe 24 is contained in a sealed pouch 26 in a sterile condition. Using proper medical procedures, the sterile gloves can be put on prior to opening the pouch 26. At that time, the pouch 26 can be opened and the syringe 24 connected to a conventional catheter tube by removal of the cap 28. Once the cap 28 has been removed, the fluid 30 contained within the barrel 29 may be discharged by depressing plunger 27. After use, the entire assembly of components can be discarded to prevent any contamination either of the patient or of those who are administering treatment.

While particular embodiments of the present invention have been illustrated and described herein, it is not intended to limit the invention and changes and modifications may be made therein within the scope of the following claims.

What is claimed is:

1. A device for use as a single use, disposable, sterile irrigation kit for catheter irrigation, comprising:
   a prefilled sterile piston syringe containing from about 45 to about 75 cc of a fluid selected from sterile water, saline solution and dilute aqueous acetic acid solutions, said syringe including a catheter tip sized to operably connect to a conventional catheter tube, a cap on said tip removably mounted to selectively prevent escape of said fluid from said syringe and prevent movement of said piston while said cap is on said tip, and kit further including a disposable pouch for enclosing said filled syringe, said pouch and said filled syringe being sterilized after enclosure of said syringe in said pouch, said device further including a container having a tear-off top labeled with the specific solution in said syringe and enclosing said pouch containing said filled syringe and further including sterilized gloves and an applicator pad.

2. The device of claim 1, wherein said fluid is selected from sterile water, a saline solution containing about 0.9% sodium chloride and a dilute aqueous acid solution containing about 0.25% acetic acid.

3. The device of claim 1, wherein said pouch and said filled syringe are sterilized using gamma radiation.

* * * * *